United States Patent
Hancock et al.

(10) Patent No.: US 10,646,138 B2
(45) Date of Patent: May 12, 2020

(54) SYSTEMS AND METHODS FOR ASSESSING ERGONOMICS UTILIZING VISUAL SENSING

(71) Applicant: The Boeing Company, Chicago, IL (US)

(72) Inventors: Glenn Alan Hancock, Saint Louis, MO (US); Tricia Hughes-Paull, Fountain Valley, CA (US); David Kanda, Huntington Beach, CA (US); Philip Specht, Huntington Beach, CA (US); Jerry Zayic, Cle Elum, WA (US)

(73) Assignee: The Boeing Company, Chicago, IL (US)

(*) Notice: Subject to any disclaimer, the term of this patent is extended or adjusted under 35 U.S.C. 154(b) by 307 days.

(21) Appl. No.: 15/132,673

(22) Filed: Apr. 19, 2016

(65) Prior Publication Data

US 2017/0296099 A1  Oct. 19, 2017

(51) Int. Cl.
*A61B 5/11* (2006.01)
*A61B 5/00* (2006.01)

(52) U.S. Cl.
CPC .............. *A61B 5/11* (2013.01); *A61B 5/1128* (2013.01); *A61B 5/4561* (2013.01); *A61B 5/0077* (2013.01); *A61B 5/742* (2013.01)

(58) Field of Classification Search
None
See application file for complete search history.

(56) References Cited

U.S. PATENT DOCUMENTS

| | | | |
|---|---|---|---|
| 2005/0151722 A1* | 7/2005 | Meteyer | G06F 3/014 345/158 |
| 2007/0276270 A1 | 9/2007 | Tran | |
| 2010/0198374 A1* | 8/2010 | Carson | G06Q 10/00 700/90 |
| 2011/0080290 A1* | 4/2011 | Baxi | A61B 5/1116 340/573.1 |
| 2012/0067255 A1* | 3/2012 | Skiba | A47B 13/00 108/102 |
| 2013/0060168 A1 | 3/2013 | Chu et al. | |
| 2013/0321579 A1* | 12/2013 | Firkus | H04N 5/247 348/46 |

(Continued)

FOREIGN PATENT DOCUMENTS

| WO | 2005120348 A1 | 12/2005 |
|---|---|---|
| WO | 2008149130 A1 | 12/2008 |

*Primary Examiner* — Ankit D Tejani (74) *Attorney, Agent, or Firm* — Miller, Matthias & Hull LLP (57) ABSTRACT

A method for assessing ergonomics of a human user in an environment is disclosed. The method includes generating a visual skeletal signal by using a visual sensor. The method further includes determining a first posture sample based on the skeletal signal, by using an electronic controller. The posture sample includes skeletal information including one or both of joint information and positioning information. The method further includes comparing the posture sample with an ergonomically ideal posture sample and determining an ergonomic report based on the comparing of the posture sample and the ergonomically ideal posture sample. The method further includes providing the ergonomic report via an output device.

20 Claims, 6 Drawing Sheets

(56) References Cited

U.S. PATENT DOCUMENTS

2014/0326084 A1* 11/2014 Bhushan .................. A61B 5/11
73/865.4
2015/0366350 A1* 12/2015 Di Censo ................ A47C 1/00
700/275

* cited by examiner

SYSTEMS AND METHODS FOR ASSESSING ERGONOMICS UTILIZING VISUAL SENSING

TECHNICAL FIELD

The present disclosure relates generally to ergonomics and, more particularly, to a systems and methods for assessing ergonomics by utilizing visual sensing techniques and apparatus.

BACKGROUND

Ergonomics is the practice of designing and/or implementing systems, products, and processes to take into account interaction between such systems, products, and processes and the human beings who use them. In practice, ergonomics may be studied to understand the interactions among human beings and other elements of an environment, such as a workplace environment. Within a workplace environment, proper use of ergonomically designed office products and/or ergonomic arrangement of the workplace may prevent employee injury, improve employee health and/or improve workplace productivity.

To collect data for studying ergonomics of a human within an environment, such as a workplace, an instructor, such as an ergonomist, may study positioning of the human user in the environment and provide feedback to the human user. However, instructors may not always be available to assess ergonomics in a given environment and/or such instructors may be cost prohibitive for the human user or his/her employer. Therefore, alternative systems and methods for ergonomics data collection, assessment, and coaching are desired.

SUMMARY

In accordance with one example, a method for assessing ergonomics for a human user in an environment is disclosed. The method includes generating a first visual skeletal signal by using a visual sensor, wherein the visual sensor monitors the human user in the environment. The method further includes determining a first posture sample based on the first skeletal signal, by using an electronic controller. The first posture sample includes skeletal information including one or both of joint information and positioning information. The method further includes comparing the first posture sample with an ergonomically ideal posture sample and determining an ergonomic report based on the comparing of the first posture sample and the ergonomically ideal posture sample, as performed by using the electronic controller. The method further includes providing the ergonomic report via an output device.

In accordance with another example, a system for assessing ergonomics of a human user in an environment is disclosed. The system includes a visual sensor configured to generate a visual skeletal signal of the human user in the environment. The system further includes an output display configured to present one or both of instructions for participating in ergonomic evaluations and an ergonomic report. The system further includes an electronic controller that includes a processor. The electronic controller is configured to receive the visual skeletal signal from the visual sensor. The electronic controller is further configured to determine a posture sample based on the visual skeletal signal, wherein the posture sample includes skeletal information, the skeletal information including one or both of joint information and positioning information. The electronic controller is further configured to compare the posture sample with an ergonomically ideal posture sample and determine the ergonomic report based on the comparison of the posture sample and the ergonomically ideal posture sample. The electronic controller is further configured to provide signals to the output display for presenting the ergonomic report.

In accordance with yet another example, a user station configured to assess ergonomics for a human user in an environment is disclosed. The user station includes a work surface and a visual display configured to present the human user with one or both of instructions for participating in ergonomic evaluation and an ergonomic report. The user station further includes a visual sensor configured to generate a visual skeletal signal of the human user in the environment and an electronic controller, which includes a processor. The electronic controller is configured to receive the visual skeletal signal from the visual sensor. The electronic controller is further configured to determine a posture sample based on the visual skeletal signal, wherein the posture sample includes skeletal information, the skeletal information including one or both of joint information and positioning information. The electronic controller is further configured to compare the posture sample with an ergonomically ideal posture sample and determine the ergonomic report based on the comparison of the posture sample and the ergonomically ideal posture sample. The electronic controller is further configured to provide signals to the output display for presenting the ergonomic report.

These and other aspects and features will become more readily apparent upon reading the following detailed description when taken in conjunction with the accompanying drawings. In addition, although various features are disclosed in relation to specific examples, it is understood that the various features may be combined with each other, or used alone, with any of the various examples without departing from the scope of the disclosure.

While the present disclosure is susceptible to various modifications and alternative constructions, certain illustrative examples thereof will be shown and described below in detail. The disclosure is not limited to the specific examples disclosed, but instead includes all modifications, alternative constructions, and equivalents thereof.

DETAILED DESCRIPTION

Reference will now be made in detail to specific examples or features, which are illustrated in the accompanying drawings. Generally, corresponding reference numbers will be used throughout the drawings to refer to the same or corresponding parts.

Figure 1:
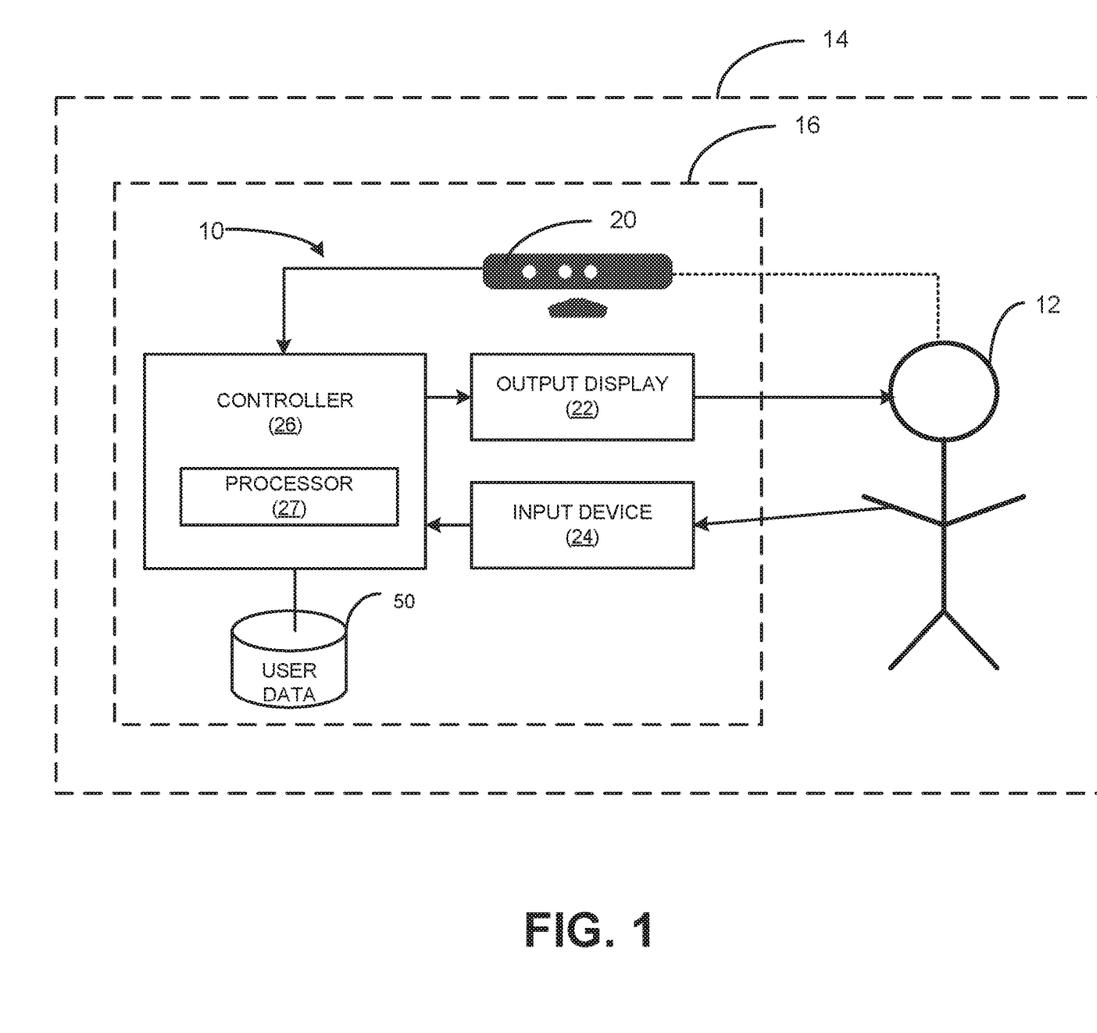
FIG. 1 is a schematic diagram of a system for assessing ergonomics for a human in an environment, in accordance with the disclosure.
Figure 2:
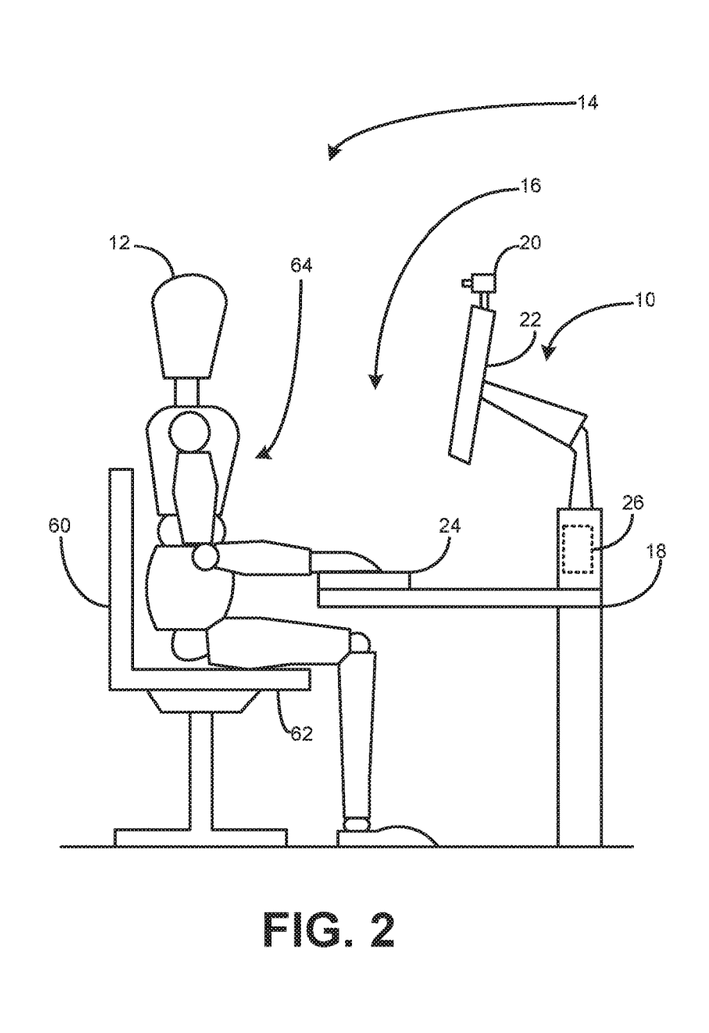
FIG. 2 is a side, diagrammatic view of an exemplary user station in which the system of FIG. 1 may be employed, in accordance with the present disclosure.
Figure 3:
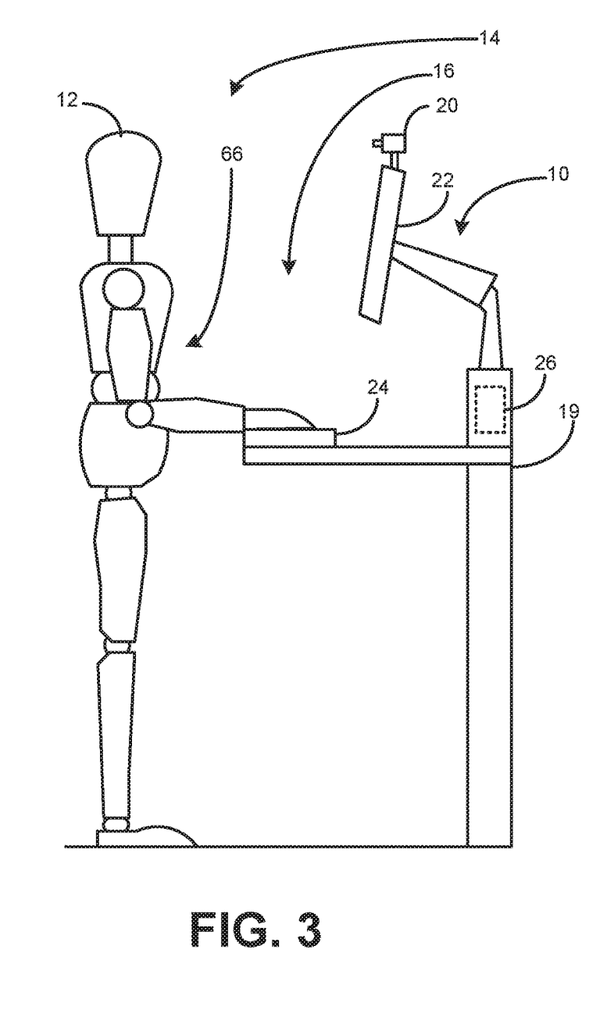
FIG. 3 is side, diagrammatic view of another exemplary user station in which the system of FIG. 1 may be employed, in accordance with the present disclosure.

FIG. 1 illustrates an exemplary system 10 for assessing ergonomics for a human user 12, within an environment 14. The environment 14 is, for example, an office environment. However, the system 10, and any system or method disclosed herein, may be utilized to assess ergonomics for a human user in any environment, such as, but not limited to, a working environment, a manufacturing environment, an educational environment, a rehabilitation environment, such as an occupational and/or physical therapy setting, or any environment within which ergonomic assessment for a human user is desired. Further, the system 10 can be integrated within a user station 16, which may include a work surface, such as a desk 18, 19, as shown in FIGS. 2 and 3, respectively, and discussed in greater detail below. The system 10 includes a visual sensor 20, an output display 22, and a controller 26, which includes, at least, a processor 27. In some examples, the system 10 includes an implement, such as an input device 24.

The visual sensor 20 is any sensor, or combination of sensors, that is configured to monitor the human user 12 in the environment 14 and generate a visual signal, such as a visual skeletal signal for the human user 12. In some examples, the visual sensor 20 is configured to obtain data as one or more of static images (e.g., a single picture), dynamic images (e.g., continuous video capture), a plurality of static images in a sequence (e.g., discrete-time image capture), and any combinations thereof. For capturing data to generate a visual skeletal signal, the visual sensor 20 may include, but is not limited to including, camera(s) 28, depth sensor(s) 30, scanners 32, lasers 34, and motion sensors 36, among other sensing devices, as shown schematically in FIG. 4. The visual sensor 20 may capture visual skeletal signals by utilizing the aforementioned sensors to track and interpret bodily position and motion of the human user 12.

Figure 4:
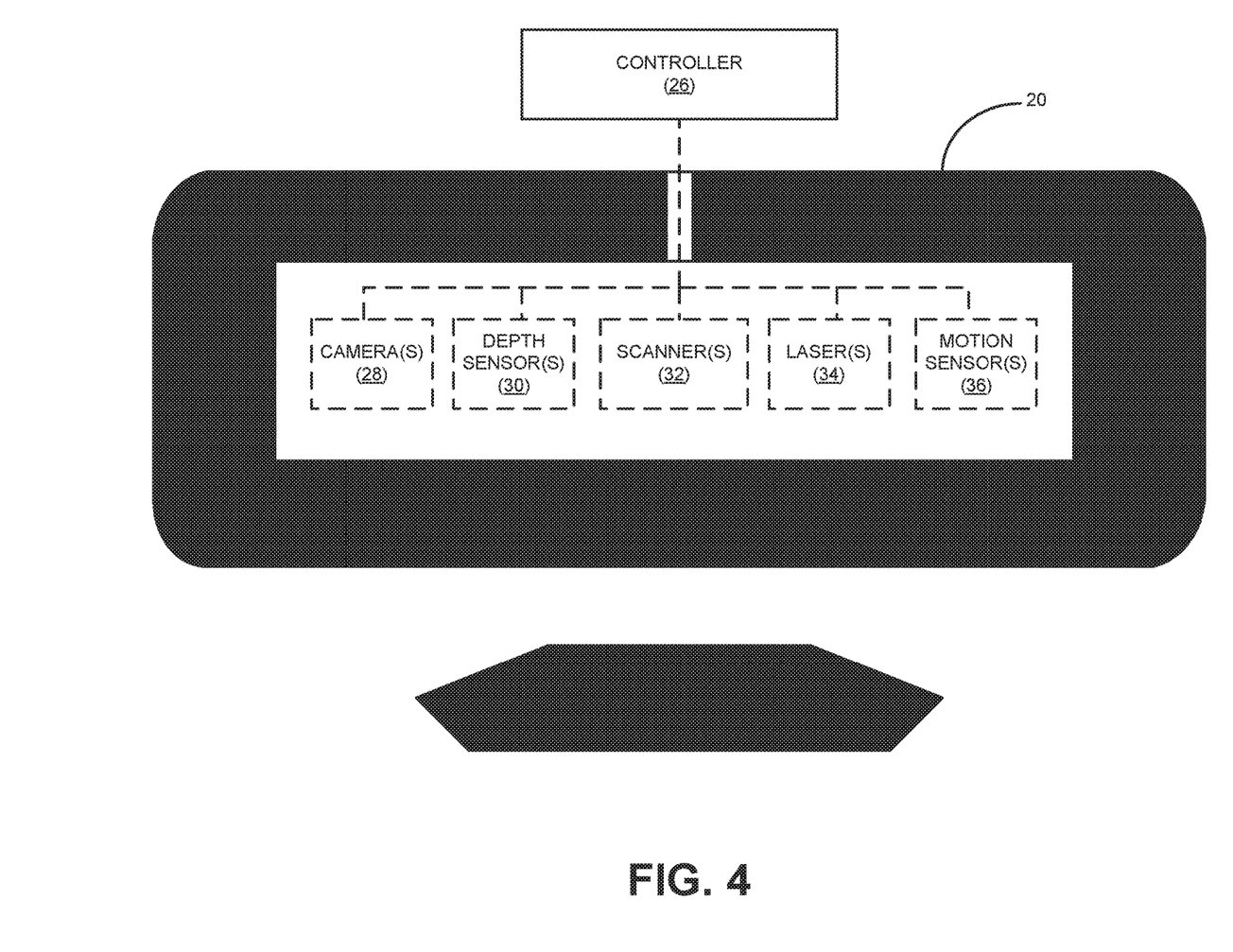
FIG. 4 is a schematic diagram of a visual sensor of the system of FIG. 1, in accordance with the example of FIG. 1.

In some examples, the camera(s) 28 includes both red-green-blue (RGB) and infrared (IR) cameras for obtaining a visual depiction of the human user 12 and/or to track motion of the human user 12, via captured images. Depth sensors 30 may be used to assess depth or distance between the human user 12 and the visual sensor 20 or depth or distance between the human user 12 and any object within visual range of the visual sensor 20, such as the output display 22 and/or a desk 18, 19. To further obtain visual and/or spatial data associated with the human user 12, the visual sensor 20 may employ the scanner(s) 32 and/or laser(s) 34 to obtain physical or three-dimensional (3-D) modelling of the human user 12, which may aide in deriving visual skeletal signals. For example, the scanner(s) 32 may include a 3-D scanning system, which obtain data associated with the human user 12 that can be employed for image-based 3-D reconstruction of the human user 12. The motion sensors 36 may be included for sensing motion in the vicinity of the visual sensor 20, which may be used, for example, to detect if the human user 12 has entered the environment 14.

Figure 5:
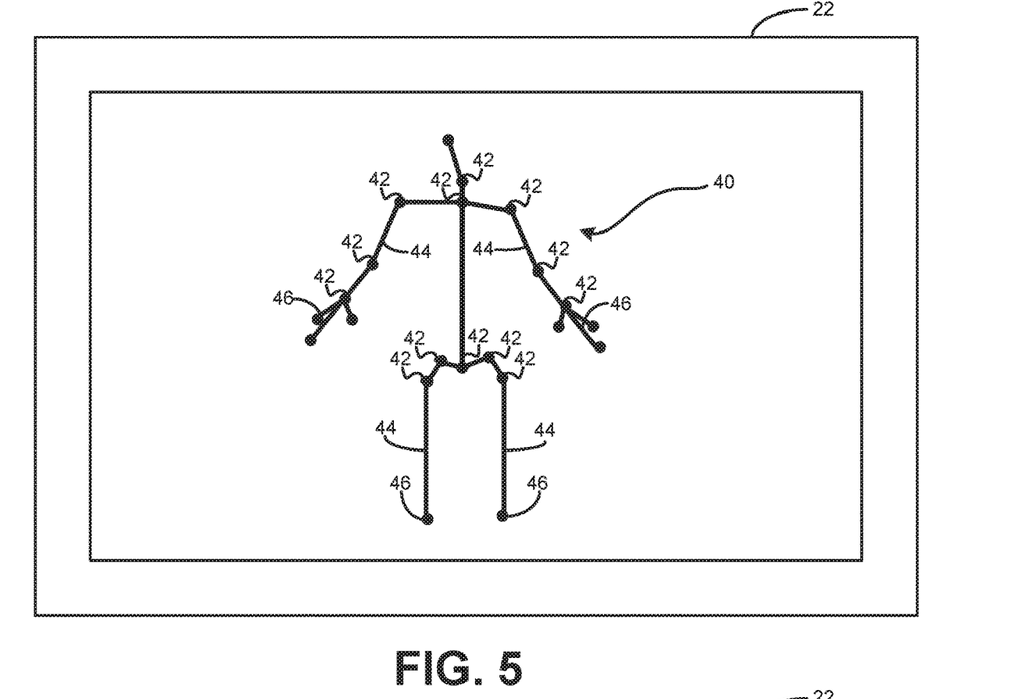
FIG. 5 is a schematic illustration of exemplary skeletal information, as displayed on an output display of the system of FIG. 1, in accordance with the system of FIG. 1.

Returning to the example illustrated at FIG. 1, the controller 26 is configured to receive signals, such as a visual skeletal signal for the human user 12, from the visual sensor 20. The controller 26 may be any electronic controller or computer, including a processor, examples of which will be discussed in greater detail, below, with reference to FIG. 8. Using the visual skeletal signal output by the visual sensor 20, the controller 26 determines a posture sample associated with the human user 12 based on the visual skeletal signal. A posture sample, as used herein, is any data sample gathered by the system 16 which includes bodily positioning information for the human user 12 and may include bodily position information gathered while the human user 12 is relatively static, in motion, and/or performing a task. The posture sample includes skeletal information, which includes, at least, joint information associated with the human user 12 and positioning information associated with the human user 12. An example of skeletal information 40 is illustrated in FIG. 5 as output to the output display 22. As shown, the skeletal information 40 includes a plurality of joint locations 42, a plurality of limb locations 44, and a plurality of extremity locations 46, among other information. Further, the skeletal information 40 shows information, or information is derived from the skeletal information, that is associated with positioning of the human user 12, relative to other items within the environment 14 (e.g., the user station 16, an implement, such as the input device 24, or any other item within the environment 14).

The posture sample, including the skeletal information, is then compared to an ergonomically ideal posture sample for the human user 12. An ergonomically ideal posture sample, as used herein, refers to a posture sample that represents a predetermined ideal ergonomic positioning of the human user 12 within the environment 14 and/or, optionally, ideal ergonomic positioning of the human user 12 while performing a task. The ergonomically ideal posture sample is determined by, but not limited to being determined by, one or more of the following methods: instructing the user on correct ergonomic posture and capturing the ideal posture sample, generating the ergonomically ideal posture sample based on baseline information for the human user 12 (e.g., height, width, limb length, etc.), and implementing an ergonomically ideal posture sample that is previously stored on a memory associated with the controller 26 such as, but not limited to, a user database 50.

Figure 6:
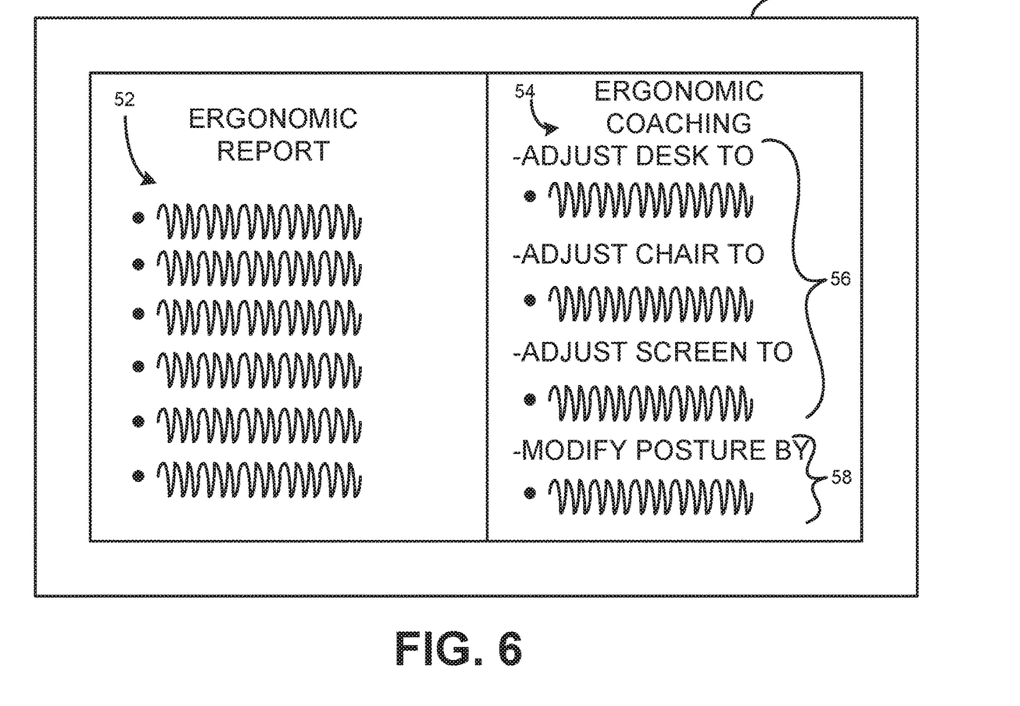
FIG. 6 is a schematic illustration of an exemplary ergonomic report and an example ergonomic coaching presentation, as displayed on the output display of the system of FIG. 1, in accordance with the system of FIG. 1.

Based on the comparison of the posture sample and the ergonomically ideal posture sample, the controller 26 determines an ergonomic report for the human user 12. As used herein, an ergonomic report encompasses information indicative of an evaluation of skeletal posture that may be presented by itself or in conjunction with a more comprehensive ergonomic assessment. The controller 26 then provides signals for presenting the ergonomic report, to the human user 12, to the output display 22. An example depiction of the output display 22, presenting an example ergonomic report 52, is shown in FIG. 6. The ergonomic report 52 includes any information related to ergonomic positioning or posture of the human user 12, the output display 22, the input device 24, or any other information for improving ergonomics in the environment 14.

In some examples, the controller 26 generates an ergonomic coaching presentation for the user based on, at least, the ergonomic report and the ergonomically ideal posture sample. The ergonomic coaching presentation includes instructions for improving posture of the human user 12, while the human user 12 is relatively static, in motion, and/or performing a task, and is presented to the human user 12, for example, via the output display 22. As shown in an exemplary ergonomic coaching presentation 54 of FIG. 6, the ergonomic coaching presentation includes coaching instructions 56 (e.g., workplace instructions) to advise the human user 12 to adjust an environmental attribute (e.g., adjusting a desk height, adjusting a monitor angle, adjusting a monitor height, adjusting a chair height, etc.). Further, in the non-limiting example of FIG. 5, the ergonomic coaching presentation 54 includes posture instructions 58 to advise the human user 12 to adjust posture or modify posture in a predetermined manner (e.g., instructions to lay feet flat on the floor, to achieve proper knee angle, to achieve proper elbow angle, to achieve safe wrist positioning relative to an implement, such as a keyboard, etc.).

In some examples, the system includes the user database 50. In such examples, controller 26 may transmit any data associated with the human user 12 (e.g., ergonomically ideal posture samples, posture samples, ergonomic reports, ergonomic coaching presentations). The user database 50 may store such user information, to be recalled by the human user 12 when desired. Alternatively, ergonomic data can be removed from the system 10, upon the human user 12 completing the report and/or coaching, to preserve privacy.

As discussed above and shown in the examples of FIGS. 2 and 3, the system 10 is employed within a user station 16 (e.g., a workstation) of the environment 14. In the exemplary depiction of the user station 16 in FIG. 3, the user station 16 includes a chair 60, which includes a seat 62. In such examples, the posture sample, from which the ergonomic report and/or coaching presentation are derived, is a seated posture sample. Alternatively, as shown in the example of FIG. 3, the user station 16 includes a standing desk 19, at which the human user 12 stands during generation of the posture sample. In such examples, the posture sample is a standing posture sample, from which an ergonomic report may be derived, such an ergonomic report including information associated with ergonomic use of the standing desk 19 (e.g., proper distance from the desk 19, feet placement, hand or wrist placement, etc.).

By utilizing the system 10 to collect ergonomics data and provide ergonomics reports and coaching presentations, ergonomics are assessed without the need for observation by an instructor, such as an ergonomist. Because the visual sensor 20 is used in conjunction with the controller 26, the system 10 may be implemented in nearly any environment wherein ergonomic assessment is desired. Further, because the system 10 does not require a third party instructor, it may monitor the human user 12 for long durations of time and provide detailed ergonomics assessment over any period of time.

Figure 7:
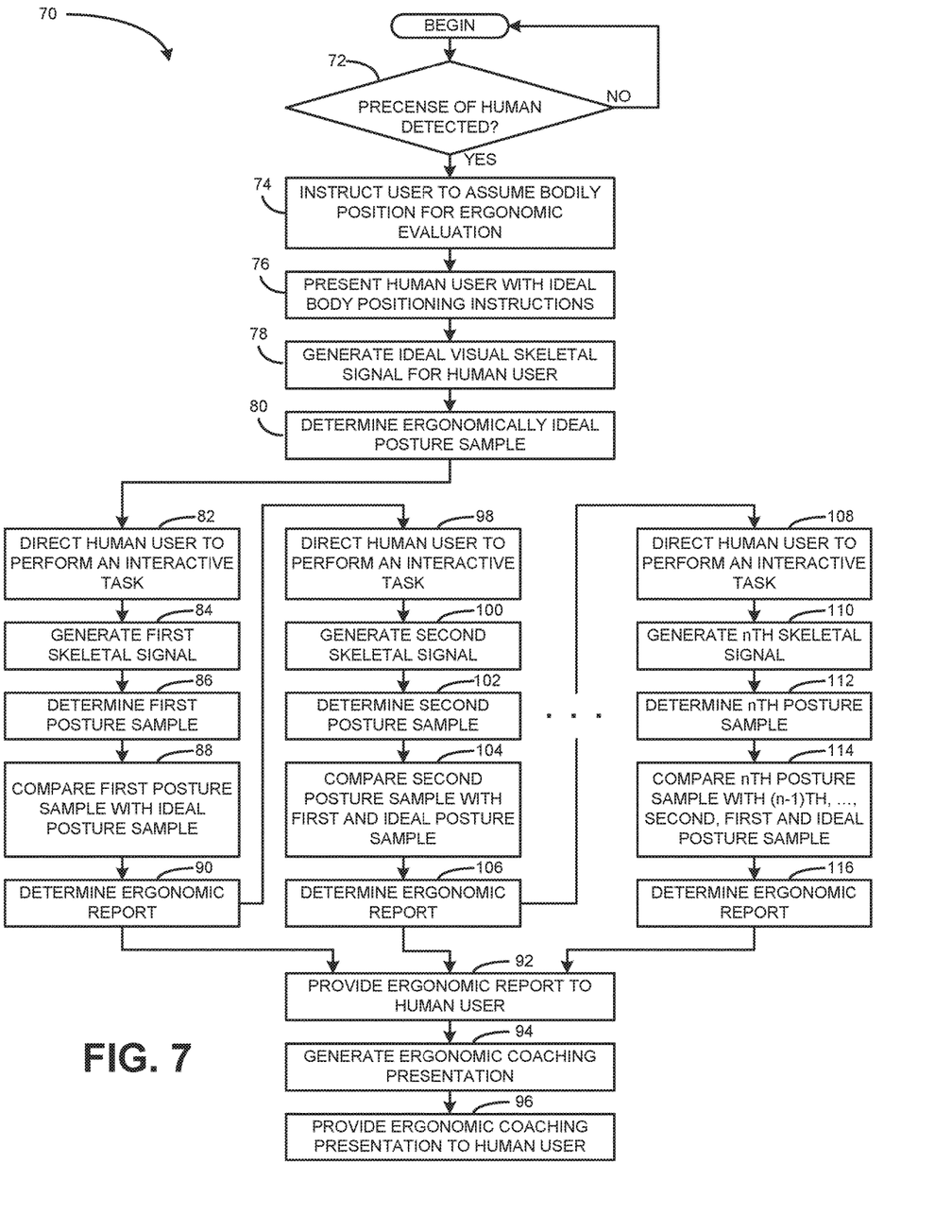
FIG. 7 is an exemplary flowchart for a method for assessing ergonomics for a human user in an environment, in accordance with the present disclosure.

Turning now to FIG. 7, a method 70 for assessing ergonomics a human user in an environment is disclosed. The method 70 will be described herein with reference to elements of the system 10 and their respective functions; however, the method 70 is certainly not limited to being implemented via the system 10 and its included elements.

In some examples, the method 70 begins at block 72, wherein the visual sensor 20 is used to detect presence of the human user 12 within the environment 14. If presence of the human user 12 is detected, the human user 12 is instructed, via bodily position instructions displayed on the output display 22 or any other output device, to assume a bodily position for ergonomic evaluation, as shown in block 74. In one example, the bodily position for ergonomic evaluation is a seated position 64 of the human user 12, as shown in FIG. 2. In an alternative example, the bodily position for ergonomic evaluation is a standing position 66, as shown in FIG. 3.

As discussed above, in certain examples, an ergonomically ideal posture sample is determined using the system 10. In such embodiments, the method 70 includes blocks 76, 78, 80. At block 76, the human user 12 is presented with ideal body positioning instructions, from which the human user 12 assumes a position specified by the ideal body positioning instructions. Then, the visual sensor 20 generates an ideal visual skeletal signal for the human user 12, as shown in block 78. Using the ideal visual skeletal signal, the controller 26 determines the ergonomically ideal posture sample based on the ideal skeletal signal, as shown in block 80. The ergonomically ideal posture sample includes ideal skeletal information, which includes one or both of ideal joint information associated with the human user 12 and ideal positioning information associated with the human user 12.

Prior to generating a first skeletal signal and deriving a first posture sample therefrom, in some examples, the method 70 includes directing the human user 12 to perform an interactive task, as shown in block 82. The directions to perform the task may be presented to the human user 12 via the output display 22; however, alternatively, the task may be presented to the human user 12 via other output devices such as speakers, lights, haptic devices, and the like. The interactive task includes stimulating the human user 12 by one or more of the following: inducing clinically significant motions by the human user 12, directing the human user 12 to perform one or more occupational maneuvers, and providing a distraction that distractsthe human user 12 and allows the subject to assume a relaxed posture for capture. One example of such a task that invokes such a response is a game played by the human user 12.

At block 84, the method 70 includes using the visual sensor 20 to generate a first visual skeletal signal for the human user 12. Using the first visual skeletal signal, the controller 26 determines a first posture sample associated with the human user 12 based on the first posture sample. As discussed above and with reference to FIG. 5, the first posture sample includes skeletal information, which includes one or both of joint information associated with the human user 12 and positioning information associated with the human user 12. In some examples, block 82 and block 84 are performed concurrently, such that the first posture sample is taken during performance of the interactive task. At block 86, the first posture sample is compared with the ideal posture sample for the human user 12, which is determined during the method 70 or is predetermined, as discussed above.

Based on the comparison of block 86, the controller 26 determines an ergonomic report. The ergonomic report is provided to the human user via, for example, the output display 22, as shown in block 92. In some examples, an ergonomic coaching presentation for the human user 12 is generated based on, at least, the ergonomic report and the ideal posture sample, as shown in block 94, which is then presented to the human user 12 via the output display 22, or any suitable output device, as shown in block 96. Examples of an ergonomic report and an ergonomic coaching presentation are shown in FIG. 6 and described above.

Returning to block 90, in some examples, a second posture sample is desired for inclusion in one or both of the ergonomic report and the ergonomic coaching presentation. In such examples, the method 70 proceeds from block 90 to block 98, wherein the human user 12 is directed to perform an interactive task. At block 98, the visual sensor 20 generates a second visual skeletal signal for the human user 12. Using the second visual skeletal signal, the controller 26 determines a second posture sample associated with the human user 12 based on the second posture sample, as shown in block 102. In some examples, block 98 and block 100 are performed concurrently, such that the first posture sample is representative of posture during performance of the interactive task.

At block 102, the second posture sample is compared with one or more of the first posture sample and the ergonomically ideal posture sample for the human user 12. Based on one or more of the second posture sample, the first posture sample, and the ergonomically ideal posture sample, the controller 26 determines the ergonomic report, as shown in block 106, which is then presented to the human user 12 at block 92. In some examples, the ergonomic report, determined at block 106, is a comparative ergonomic report, comparing and/or contrasting amongst two or more of the first posture sample, the second posture sample, and the ergonomically ideal posture sample. The comparative ergonomic report includes information regarding changes in posture of the human user 12 between the first and second posture samples. Then, the method 70 may proceed to block 92 or block 108.

The steps of generating additional posture samples for data inclusion in the ergonomic report may be repeated any number of times (e.g., "n" times). As such, if more than two posture samples in addition to the ergonomically ideal posture sample are desired, the method 70 continues, from block 106, to block 108. At block 108, the human user 12 is directed to perform an interactive task. At block 110, the visual sensor 20 generates an nth visual skeletal signal for the human user 12. Using the nth visual skeletal signal, the controller 26 determines a nth posture sample associated with the human user 12 based on the nth posture sample, as shown in block 112. In some examples, block 108 and block 110 are performed concurrently, such that the nth posture sample is representative of posture during performance of the interactive task.

At block 114, the nth posture sample is compared with one or more of the first posture sample and the ergonomically ideal posture sample for the human user 12. Based on one or more of the nth posture sample, a (n−1)th posture sample, any of a (n−1)th through the second posture samples, the first posture sample, and the ergonomically ideal posture sample, the controller 26 determines the ergonomic report, as shown in block 116, which is then presented to the human user 12 at block 92.

It is to be understood that the flowchart of FIG. 6 is shown and described as an example only to assist in disclosing the features of the disclosed system and techniques, and that more or less steps than that shown may be included in the process corresponding to the various features described above for the disclosed system without departing from the scope of the disclosure.

Figure 8:
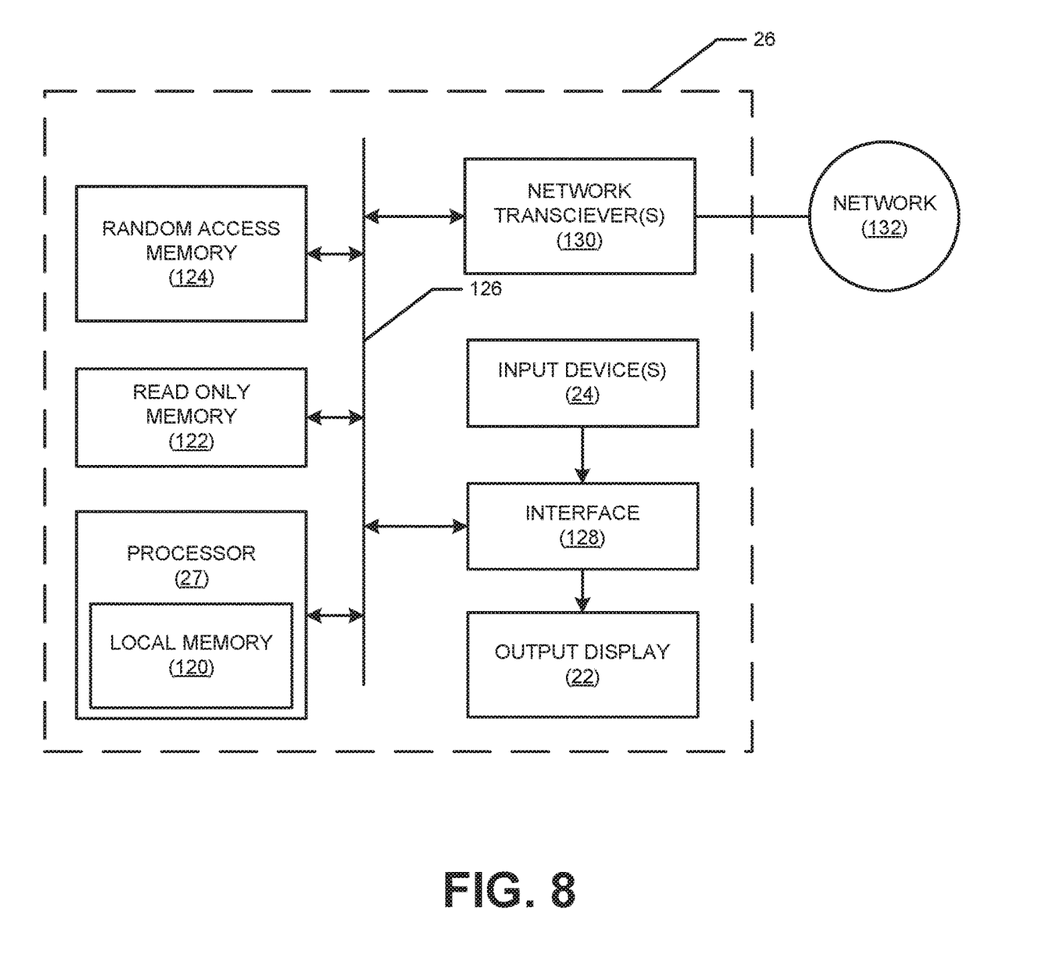
FIG. 8 is a schematic diagram for an exemplary computer that may execute instructions for providing the exemplary systems and methods of the present disclosure.

FIG. 8 schematically illustrates a combination of example elements which may be used to implement the controller 26 of the system 10, as shown in FIG. 1. The exemplary controller 26 is capable of executing instructions to realize the functions of the system 10 and/or execute instructions to perform the method 70, discussed above in reference to FIGS. 5-6. The controller 26 may be, for example, a server, a personal computer, or any other type of computing device. The controller 26 of the instant example includes the processor 27. For example, the processor 27 may be implemented by one or more microprocessors or controllers from any desired family or manufacturer.

The processor 27 includes a local memory 120 and is in communication with a main memory including a read only memory 122 and a random access memory 124 via a bus 126. The random access memory 124 may be implemented by Synchronous Dynamic Random Access Memory (SDRAM), Dynamic Random Access Memory (DRAM), RAMBUS Dynamic Random Access Memory (RDRAM) and/or any other type of random access memory device. The read only memory 122 may be implemented by a hard drive, flash memory and/or any other desired type of memory device.

In some examples, the controller 26 includes an interface circuit 128. The interface circuit 128 may be implemented by any type of interface standard, such as, for example, an Ethernet interface, a universal serial bus (USB), and/or a PCI express interface. One or more input devices 24 are connected to the interface circuit 128. The input device(s) 24 permit a user to enter data and commands into the processor 27. The input device(s) 24 can be implemented by, for example, a keyboard, a mouse, a touchscreen, a track-pad, a trackball, and/or a voice recognition system. For example, the input device(s) 24 may include any wired or wireless device for connecting inputting data in to the controller 26 in response to an interactive task, as described in blocks 82, 98, and 108 of the method 70 of FIG. 7.

The output display 22 is also connected to the interface circuit 128. The output display 22 is implemented by, for example, display devices for associated data (e.g., a liquid crystal display, a cathode ray tube display (CRT), etc.).

Further, in some examples, the controller 26 includes one or more network transceivers 130 for connecting to a network 132, such as the Internet, a WLAN, a LAN, a personal network, or any other network for connecting the controller 26 to one or more other controllers or network capable devices. As such, the controller 26 may be embodied by a plurality of controllers 26 for controlling various elements of the system 10.

As mentioned above the controller 26 may be used to execute machine readable instructions. For example, the controller 26 executes machine readable instructions to perform the method 70 shown in the block diagrams of FIG. 7. In such examples, the machine readable instructions comprise a program for execution by a processor, such as the processor 27, shown in the example controller 26. The program may be embodied in software stored on a tangible computer readable medium such as a CD-ROM, a floppy disk, a hard drive, a digital versatile disk (DVD), a Blu-ray disk, or a memory associated with controller 26, but the entire program and/or parts thereof could alternatively be executed by a device other than the processor 27 and/or embodied in firmware or dedicated hardware. Further, although the example programs are described with reference to the flowcharts illustrated in FIG. 7, many other methods of implementing examples of the present disclosure may alternatively be used. For example, the order of execution of the blocks may be changed, and/or some of the blocks described may be changed, eliminated, or combined.

While the foregoing detailed description has been given and provided with respect to certain specific examples, it is to be understood that the scope of the disclosure should not be limited to such examples, but that the same are provided simply for enablement and best mode purposes. The breadth and spirit of the present disclosure is broader than the examples specifically disclosed and encompassed within the claims appended hereto. Moreover, while some features are described in conjunction with certain specific examples, these features are not limited to use with only the example with which they are described, but instead may be used together with or separate from, other features disclosed in conjunction with alternate examples.

What is claimed is:

1. A method for assessing ergonomics of a human user in an environment, the method comprising:
   prompting the human user via an output device to perform an interactive task;
   generating, using a visual sensor that monitors the human user in the environment, a first visual skeletal signal while the human user performs the interactive task;
   determining, using an electronic controller, a first posture sample based on the first visual skeletal signal, the first posture sample including skeletal information, the skeletal information including one or both of joint information and positioning information;
   comparing, using the electronic controller, the first posture sample with an ergonomically ideal posture sample, the ergonomically ideal posture sample being specific to the human user alone;
   determining, using the electronic controller, an ergonomic report based on the comparing of the first posture sample and the ergonomically ideal posture sample; and
   providing the ergonomic report via an output device.

2. The method of claim 1, further comprising:
   generating, using the visual sensor, an ideal visual skeletal signal; and
   determining, using the electronic controller, the ergonomically ideal posture sample based on the ideal skeletal signal, the ergonomically ideal posture sample including ideal skeletal information, the ideal skeletal information including one or both of ideal joint information and ideal positioning information associated with the human user.

3. The method of claim 2, further comprising presenting ideal body positioning instructions, via the output device, for generating the ideal visual skeletal signal.

4. The method of claim 1, wherein generating the first visual skeletal signal includes capturing at least one of a static image, a dynamic image of the human user, a plurality of static images captured in sequence, and combinations thereof.

5. The method of claim 1, further comprising:
   detecting presence of the human user within the environment, using the visual sensor; and
   in response to detecting presence, displaying, via the output device, ideal body position instructions.

6. The method of claim 5, wherein displaying the ideal body position instructions further includes displaying one of an ideal standing position instruction and an ideal seated position instruction.

7. The method of claim 1, wherein prompting the interactive task includes one or more of prompting clinically significant motions, prompting one or more occupational maneuvers, and prompting a distraction.

8. The method of claim 1, further comprising:
   generating, using the visual sensor, a second visual skeletal signal associated with the human user;
   determining, using the electronic controller, a second posture sample based on the second visual skeletal signal, the second posture sample including second skeletal information, the second skeletal information including one or both of joint information and positioning information;
   comparing, using the electronic controller, the first posture sample, the second posture sample, and the ergonomically ideal posture sample;
   determining a comparative ergonomic report based on the comparing of the first posture sample, second posture sample, and the ergonomically ideal posture sample; and
   displaying the comparative ergonomic report via the output device, the comparative ergonomic report including information regarding changes in posture of the human user between the first and second posture samples.

9. The method of claim 1, further comprising generating, using the electronic controller, an ergonomic coaching presentation based on, at least, the ergonomic report and the ergonomically ideal posture sample, the ergonomics coaching presentation including instructions for improving posture of the human user; and
   displaying the ergonomic coaching presentation via the output device.

10. The method of claim 9, wherein generating the ergonomic coaching presentation includes generating coaching instructions for the ergonomics coaching presentation, the coaching instructions including one or more of instructions for adjusting positioning of a desk, instructions for adjusting positioning of a chair, instructions for adjusting positioning of the output device, and instructions for modifying the posture of the human user in a predetermined manner.

11. The method of claim 1, wherein the visual sensor includes one or more of a camera, a depth sensor, a scanner, a laser, and a motion sensor.

12. A system for assessing ergonomics of a human user in an environment, the system comprising:
   a visual sensor configured to generate a visual skeletal signal of the human user in the environment;
   an output display configured to present one or both of instructions for participating in ergonomic evaluations and an ergonomic report;
   an electronic controller including a processor and configured to
      display a prompt for the human user to perform an interactive task, wherein generation of the visual skeletal signal is performed by the visual sensor while the human user performs the interactive task;
      receive the visual skeletal signal from the visual sensor,
      determine a posture sample based on the visual skeletal signal, the posture sample including skeletal information, the skeletal information including one or both of joint information and positioning information,
      compare the posture sample with an ergonomically ideal posture sample, the ergonomically ideal posture sample being specific to the human user alone,
      determine the ergonomic report based on the comparing of the posture sample and the ergonomically ideal posture sample, and
      provide signals, to the output display, for presenting the ergonomic report to the human user.

13. The system of claim 12, further comprising a database configured to receive human user information from the electronic controller and store the human user information, the user information including, at least, the posture sample.

14. The system of claim 12, wherein the visual sensor includes one or more of a camera, a depth sensor, a scanner, a laser, and a motion sensor.

15. A user station configured to assess ergonomics of a human user in an environment, the user station including:
   a work surface disposed in the environment;

a visual display configured to present the human user with one or both of instructions for participating in ergonomic evaluation and an ergonomic report, as well as a prompt to perform a task;

a visual sensor configured to generate, at least, a visual skeletal signal of the human user at the work surface in the environment while the human user performs the task;

an electronic controller, including a processor, configured to
- receive the visual skeletal signal from the visual sensor,
- determine a posture sample based on the visual skeletal signal, the posture sample including skeletal information, the skeletal information including one or both of joint information and positioning information,
- compare the posture sample with an ergonomically ideal posture sample, the ergonomically ideal posture sample being specific to the human user alone,
- determine the ergonomic report based on the comparison of the posture sample and the ergonomically ideal posture sample, and
- provide signals to the visual display for presenting the ergonomic report.

16. The user station of claim 15, further comprising a chair including a seat, configured to support the human user during generation of the posture sample, wherein the posture sample is a seated posture sample, and wherein the ergonomic report includes information associated with the chair.

17. The user station of claim 16, wherein the information associated with the chair includes instructions for adjusting a height of the chair.

18. The user station of claim 16, wherein the visual sensor includes one or more of a camera, a depth sensor, a scanner, a laser, and a motion sensor.

19. The user station of claim 15, wherein the work surface is a standing desk at which the human user stands during generation of the posture sample, wherein the posture sample is a standing posture sample, and wherein the ergonomic report includes information associated with ergonomic use of a standing desk.

20. The user station of claim 15, further comprising a database configured to receive human user information from the electronic controller and store the human user information, the user information including, at least, the posture sample.

* * * * *